United States Patent [19]

Fukui

[11] Patent Number: 4,653,926
[45] Date of Patent: Mar. 31, 1987

[54] METHOD OF DETECTING BLURRED PHOTOGRAPHIC ORIGINALS

[75] Inventor: Takashi Fukui, Minamiashigara, Japan

[73] Assignee: Fuji Photo Film Co., Ltd., Kanagawa, Japan

[21] Appl. No.: 497,154

[22] Filed: May 23, 1983

Related U.S. Application Data

[63] Continuation-in-part of Ser. No. 251,099, Apr. 6, 1981, abandoned.

[51] Int. Cl.⁴ .............................................. G01N 21/59
[52] U.S. Cl. ....................................... 356/444; 355/77
[58] Field of Search ................ 356/443, 444, 432–435, 356/71; 250/201 AF; 355/55, 56, 79; 354/401, 404, 407

[56] References Cited

U.S. PATENT DOCUMENTS

| | | | |
|---|---|---|---|
| 3,709,613 | 1/1973 | Zahn et al. | 356/443 |
| 3,856,417 | 12/1974 | Bey et al. | 356/443 X |
| 3,981,579 | 9/1976 | Weinert et al. | 356/444 X |
| 3,984,184 | 10/1976 | Pflugbeil | 356/444 X |
| 4,001,594 | 1/1977 | Akimoto et al. | 356/443 X |
| 4,542,984 | 9/1985 | Shiota et al. | 356/125 X |

Primary Examiner—Vincent P. McGraw

[57] ABSTRACT

The transmission density of a photographic original is measured at parts thereof using a pair of light measuring systems having different measuring areas. A characteristic value of the frequency distribution of the difference between measured transmission densities obtained from the pair of light measuring systems is used to distinguish blurred images from sharp images.

8 Claims, 10 Drawing Figures

METHOD OF DETECTING BLURRED PHOTOGRAPHIC ORIGINALS

This application is a continuation-in-part application of application Ser. No. 251,099 filed Apr. 6, 1981 now abandoned.

BACKGROUND OF THE INVENTION

1. Field of the Invention

This invention relates to a method of detecting a blurred image, and more particularly to a method of determining whether or not an image recorded on a photographic film is blurred.

2. Description of the Prior Art

When printing photographs from photographic originals, originals having blurred or unfocused images should be excluded.

There have been proposed various methods of detecting a blurred image or a blurred photographic original among a number of originals. For example, in one of the methods, the image of the original is subjected to Fourier transform and the spectral components thereof are examined if they are higher than a predetermined frequency to know if they are blurred. In order to carry out an optical Fourier transform, an expensive sophisticated system is needed. On the other hand, when carrying out an electrical Fourier transform, there is a difficulty in that there is not a high-speed Fourier-transform element capable of matching with the printing speed of an original photographic printer.

In another method, an original is scanned to obtain the maximum density gradient in a high frequency range of the image of the original and the maximum density gradient of the image which has been processed to be unsharp by removing therefrom high spatial frequency components are compared and operated to obtain the quotient thereof. Whether or not the original is blurred is determined by comparing the quotient with a threshold value. This is disclosed in Japanese Unexamined Patent Publication No. 53(1978)-70428. However, this method is disadvantageous in that an apparatus for carrying out the method would be complicated since it necessitates circuits for detecting the maximum value and calculating the quotient.

SUMMARY OF THE INVENTION

In light of the foregoing observation and description, the primary object of the present invention is to provide a method of and an apparatus for detecting a blurred image which is free from the drawbacks mentioned hereinabove.

In accordance with the present invention, a photographic original is scanned and the transmissivity or the transmission density of the original is measured using two light measuring systems the measuring areas of which are different from each other. The transmissivity or the transmission density measured by one light measuring system is compared with that measured by the other light measuring system to obtain the difference therebetween. Whether or not the original is blurred is determined based on the frequency distribution of the difference. For example, when the frequency distribution is comparatively flat over a range of difference in density, the original is determined to be blurred.

Generally, when taking a picture, the focus is adjusted to the principal subject matter. Further, it can be said statistically that the principal subject matter is generally positioned at the middle of the image, especially in photographs taken by amateurs. Therefore, it is preferred to scan the middle portion of the image for detecting blurred originals.

DETAILED DESCRIPTION OF THE INVENTION

Figure 1A:
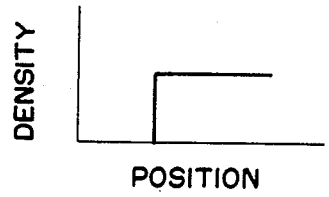
FIG. 1A is a graph showing the density curve in a sharp image by way of example.
Figure 1B:
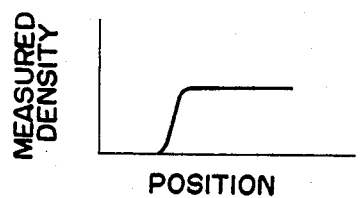
FIG. 1B is a graph showing the curve of the measured density obtained by the measuring system having a smaller measuring area when the image represented by the curve of FIG. 1A is measured.
Figure 1C:
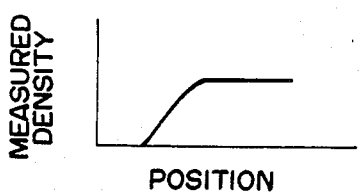
FIG. 1C is a graph showing the curve of the measured density obtained by the measuring system having a larger measuring area when the image represented by the curve of FIG. 1A is measured.

In case of a sharp image, density changes sharply at edges of a pattern of the image as represented by a density curve shown in FIG. 1A. When the density of the sharp image represented by the density curve of FIG. 1A is measured using a pair of light measuring systems having different measuring areas (the area of each scanning spot), the measured density obtained by the light measuring system having the smaller measuring area changes relatively sharply as shown in FIG. 1B, while the measured density obtained by the light measuring system of the larger measuring area changes gently as shown in FIG. 1C. For example, the larger measuring area may be 1 mm square (as measured on the original), while the smaller measuring area may be 0.1 mm square. The light measuring system having a measuring area of 0.1 mm square can pick up the frequency components of the image up to 20 c/mm, while the light measuring system having a measuring area of 1 mm square can pick up the frequency components up to 2 c/mm.

Figure 1D:
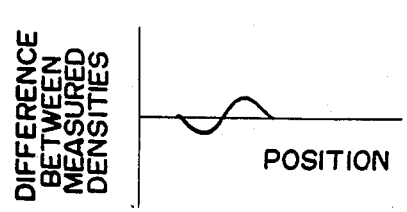
FIG. 1D is a graph showing the difference between the measured densities of FIGS. 1B and 1C.

The difference between the two measured densities obtained by the pair of light measuring systems having different measuring areas gives a curve (referred to as a density difference curve hereinafter) as shown in FIG. 1D by way of example. Generally, the difference between the two measured densities is large in case of a sharp image. Accordingly, in case of a sharp image, the amplitude of the density difference curve is large.

Figure 2A:
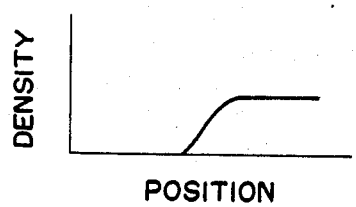
FIG. 2A is a graph showing the density curve in a blurred image by way of example.
Figure 2B:
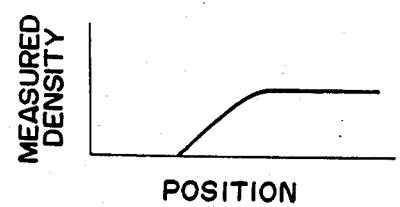
FIG. 2B is a graph showing the curve of the measured density obtained by the measuring system having a smaller measuring area when the image represented by the curve of FIG. 2A is measured.
Figure 2C:
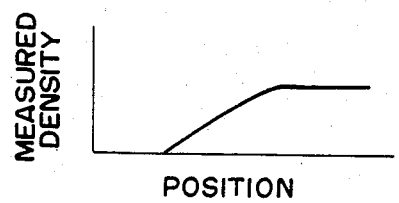
FIG. 2C is a graph showing the curve of the measured density obtained by the measuring system having a larger measuring area when the image represented by the curve of FIG. 2A is measured.
Figure 2D:
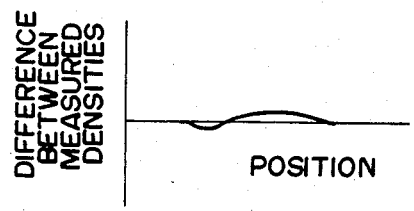
FIG. 2D is a graph showing the difference between the measured densities of FIGS. 2B and 2C.

On the other hand, in case of a blurred image density changes gently at edges of a pattern of the image as represented by a density curve shown in FIG. 2A. Accordingly, both the measured densities obtained by the pair of light measuring systems having different measuring areas will change relatively gently as shown in FIGS. 2B and 2C. Then, the density difference curve will be as shown in FIG. 2D.

The differences between the measured densities are sampled, and the number of the sampled spots having density within predetermined ranges is counted for each range. Then a frequency distribution curve (histogram) shown in a solid line 1 in FIG. 3 is obtained in case of the sharp image, while a frequency distribution curve shown in a dotted line 2 in FIG. 3 is obtained in case of the blurred image.

Figure 3:
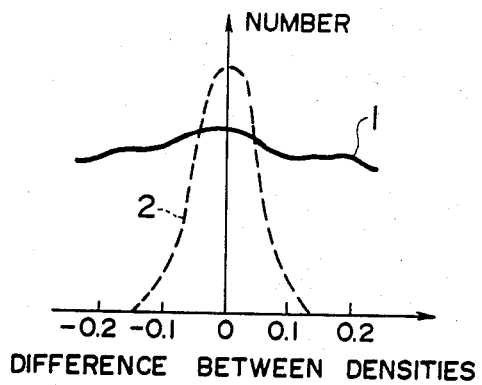
FIG. 3 is a histogram showing the frequency distribution of the difference between measured densities in which the abscissa represents the difference between the outputs of the two light measuring systems and the ordinate represents the frequency (number of spots detected)

As can be seen from FIG. 3, the frequency distribution curve of the sharp image is materially different from that of the blurred image. Accordingly, whether or not the image is blurred can be determined by using a characteristic value which can distinguish the frequency distribution of the blurred image from that of the sharp image.

As the characteristic value, the difference or the ratio between accumulated frequency of $-0.15 \leq \Delta D \leq 0.15$ and accumulated frequency of $\Delta D \leq -0.15$, $\Delta D \geq 0.15$, for example, can be used, wherein $\Delta D$ represents the difference between the measured densities. In this case, whether or not the image is blurred is determined depending upon whether or not the above difference or ratio is smaller or larger than a predetermined threshold value. Otherwise, the frequency of a predetermined difference between the measured densities can be used as the characteristic value. Further, the frequency at the peak of the frequency distribution curve, the ratio of the frequency at the peak to the frequency at a certain value of the difference between the measured densities, or the area of a zone between the frequency distribution curve and the abscissa within a certain region in the frequency distribution curve may be used as the characteristic value.

Figure 4:
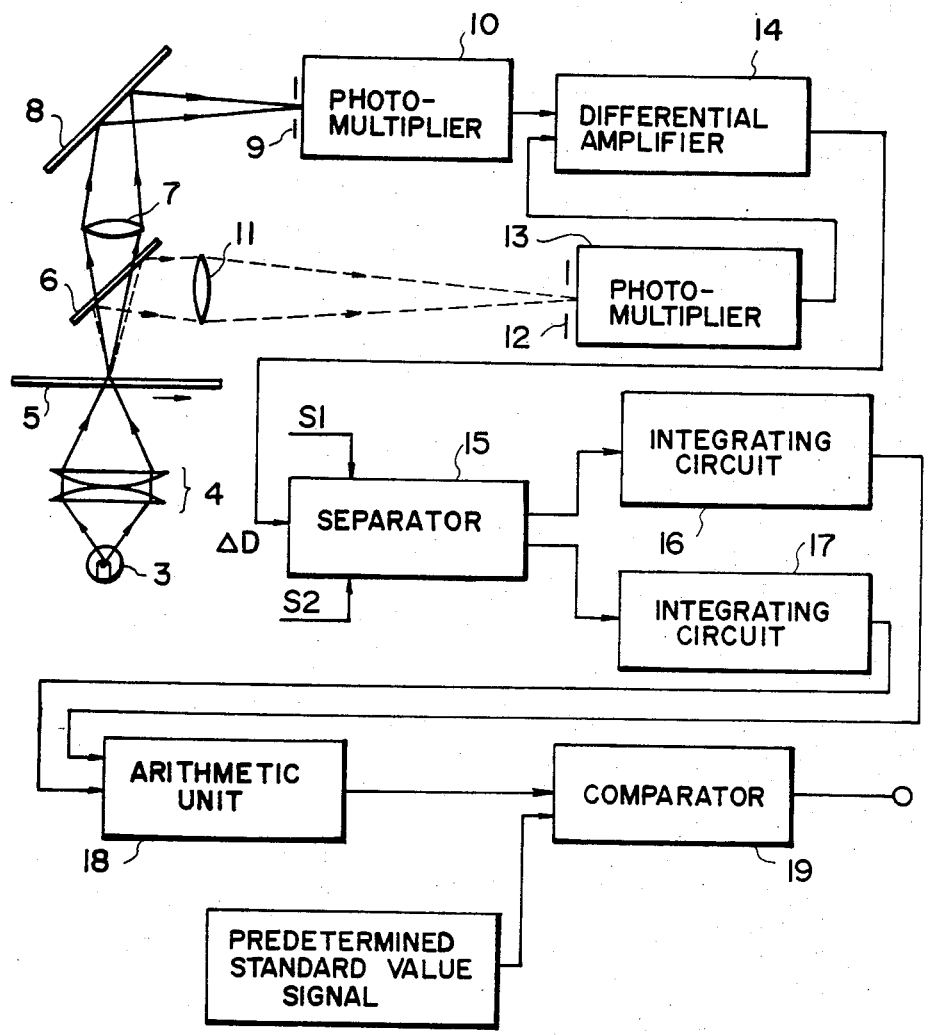
FIG. 4 is a schematic view showing an apparatus for carrying out the method of the present invention.

Now referring to FIG. 4 which schematically shows, by way of example, an apparatus for carrying out the method of the present invention, light emitted by a light source 3 illuminates a photographic original 5 having a transmission type image from below through a condenser lens system 4. The original 5 is moved in the direction indicated by an arrow to be scanned by the light. Practically, the original is two-dimensionally scanned, although it is not clearly illustrated in FIG. 4.

The light passing through the original 5 is divided into two components by means of a half-silvered mirror 6. The light component passing through the half-silvered mirror 6 travels through a lens 7 and is reflected by a mirror 8 to enter a first photomultiplier 10 through a first mask 9 to be converted into an electric signal. The other component reflected by the half-silvered mirror 6 enters a second photomultiplier 13 through a lens 11 and a second mask 12 to be converted into an electric signal.

The lenses 7 and 11 are located at the positions to form images of the masks 9 and 12 on the original 5, respectively. When the magnifying power of the lenses 7 and 11 is 1/10 and the size of the apertures of the masks 9 and 12 are 1 mm square and 10 mm square, respectively, the measuring areas of the first and second photomultipliers 10 and 13 on the original 5 are 0.1 mm square and 1 mm square, respectively.

The signal outputs from said photomultipliers 10 and 13 are directly transmitted to a differential amplifier 14 in case of effecting calculation based on the transmissivity and via a log conversion circuit (not shown) in case of effecting calculation based on the density. The differential amplifier 14 calculates the difference between the signals. The output signal or a difference signal $\Delta D$ from the differential amplifier 14 is put into a separator 15 together with predetermined value signals S1 and S2, whereby the difference signal $\Delta D$ is divided into two groups in comparison with the predetermined value signals S1 and S2. For example, the signals S1 and S2 corresponds to predetermined values of the difference, e.g. $-0.15$ and $0.15$, with reference to which the difference signal $\Delta D$ should be divided into groups. The two groups of signals are put into integrating circuits 16 and 17, respectively, wherein the sum of the difference signals $\Delta D$ of each group is obtained to provide an accumulated frequency for each group.

That is, the integrating circuit 16 takes the sum of the signals within a range of $-0.15 \leq \Delta D \leq 0.15$, and the integrating circuit 17 takes the sum of the signals outside the range. The accumulated frequencies within the range and outside the range thus obtained are transmitted to an arithmetic unit 18 where the ratio or difference of the two accumulated frequencies is obtained. The obtained value is further sent to a comparator 19 where it is compared with a predetermined standard value signal. The comparator 19 outputs a signal indicating that the image is sharp when the ratio is larger than the predetermined value while otherwise outputs a signal indicating that the image is blurred. Thus, the frequency distribution can be obtained.

Generally, the peak values of the frequency distribution of the density difference is at the point of zero difference ($\Delta D = 0$) as seen in FIG. 3 and cannot be at other positions. Therefore, the signal, e.g. signal S1 put into the separator 15, provides a zero value of the difference corresponding to the peak value. Thus, for example, a signal of zero difference put into the separator 15 is forwarded to one of the integrating circuit 16.

I claim:

1. A method of detecting a blurred image comprising the steps of:
   measuring the transmission density of a photographic original at parts thereof using a first light measuring system having a first area of measurement on the original,
   measuring the transmission density of said photographic original at parts thereof using a second light measuring system having a second area of measurement on the original larger than said first area of measurement and overlapping said first area of measurement,
   comparing the outputs of said first and said second light measuring systems with each other, and
   determining that the image on the photographic original is blurred depending on whether or not a characteristic value of the frequency of the difference between the measured densities obtained from the pair of light measuring systems is smaller than a predetermined value.

2. A method as defined in claim 1 wherein said characteristic value is a ratio of an accumulated frequency of said difference between the measured densities within a predetermined range to an accumulated frequency of the difference outside the predetermined range.

3. A method as defined in claim 1 wherein said characteristic value is a difference between an accumulated frequency of said difference between the measured densities within a predetermined region and an accumulated frequency of the difference outside the predetermined range.

4. A method as defined in claim 1 wherein said characteristic value is a value of the frequency of a predetermined value of the difference.

5. A method as defined in claim 1 wherein said characteristic value is the value of the frequency at the zero value of the difference.

6. A method as defined in claim 1 wherein said characteristic value is a ratio of the frequency at the zero value of difference to the frequency at a predetermined value of the difference between the measured values.

7. A method as defined in claim 1 wherein said characteristics value is the difference between the frequency at the zero value of the difference and the frequency at a predetermined value of the difference between the measured values.

8. A method as defined in any one of claims 1 to 7 wherein said transmission density of a photographic original is measured at a middle part of the photographic original.

* * * * *